US008734491B2

(12) United States Patent
Seavey (10) Patent No.: US 8,734,491 B2
(45) Date of Patent: May 27, 2014

(54) METHOD AND APPARATUS FOR THE STABILIZATION OF THE TRAPEZIOMETACARPAL JOINT

(75) Inventor: Jeffrey F. Seavey, Houston, TX (US)

(73) Assignee: Instratek, Inc., Houston, TX (US)

( * ) Notice: Subject to any disclaimer, the term of this patent is extended or adjusted under 35 U.S.C. 154(b) by 278 days.

(21) Appl. No.: 13/216,550

(22) Filed: Aug. 24, 2011

(65) Prior Publication Data

US 2013/0053897 A1 Feb. 28, 2013

(51) Int. Cl.
*A61B 17/80* (2006.01)
(52) U.S. Cl.
USPC .......................................... 606/280; 606/232
(58) Field of Classification Search
USPC ................ 606/148, 232, 233, 280, 281
See application file for complete search history.

(56) References Cited

U.S. PATENT DOCUMENTS

| 5,645,605 | A | 7/1997 | Klawitter |  |
|---|---|---|---|---|
| 6,702,772 | B1 | 3/2004 | Colditz |  |
| 7,875,058 | B2 * | 1/2011 | Holmes, Jr. | 606/232 |
| 8,021,431 | B1 | 9/2011 | Townley |  |
| 8,221,455 | B2 * | 7/2012 | Shurnas et al. | 606/232 |
| 2009/0005871 | A1 | 1/2009 | White et al. |  |
| 2009/0012617 | A1 | 1/2009 | White et al. |  |
| 2010/0168864 | A1 | 7/2010 | White et al. |  |
| 2010/0324694 | A1 | 12/2010 | Hassler et al. |  |
| 2011/0054627 | A1 | 3/2011 | Bear |  |
| 2011/0190887 | A1 | 8/2011 | Shapiro |  |
| 2011/0295379 | A1 | 12/2011 | Shohat |  |
| 2012/0016483 | A1 | 1/2012 | White et al. |  |
| 2013/0245700 | A1 * | 9/2013 | Choinski | 606/300 |

OTHER PUBLICATIONS

Taghinia Amir H, Suture Anchor Suspension and Fascia Lata Interposition Arthroplasty for Basal Joint Arthiritis of the Thumb, Plast Reconstr Surg. Aug. 2008, 497-504.*
Bufalini Carlo, Distraction Arthroplasty of the Trapeziometacarpal Joint, Journal of Hand Surgery 32.9, Nov. 2007, 1443-1446.*
Bernstein Matthew, Base of Thumb Metacarpal Fractures, Key Techniques in Orthopaedic Sugery, 2000, 86-91.*
Wehbe Marwan, Trapexium Resection with Mersilene Suspension Sling, Hand Clinics, vol. 29 Issue 1, Feb. 2013, 27-35.*
Instratek Incorporated, CMC Cable Fix, 2011, Instratek Incorporated, all pages.*

* cited by examiner

*Primary Examiner* — Nicholas Woodall
(74) *Attorney, Agent, or Firm* — Barnes & Thornburg LLP (57) ABSTRACT

A method and apparatus for the stabilization of the trapeziometacarpal joint following the removal or partial resection of the trapezium includes an assembly for securing a first metacarpal relative to a second metacarpal. The assembly includes a suture guide having a suture anchor plate that is frangibly connected to a guide stem.

20 Claims, 9 Drawing Sheets

METHOD AND APPARATUS FOR THE STABILIZATION OF THE TRAPEZIOMETACARPAL JOINT

BACKGROUND

The present invention relates generally to surgical repair of the trapeziometacarpal joint. More specifically, the present invention relates to a method and apparatus for the stabilization of the trapeziometacarpal joint following the removal or partial resection of the trapezium.

The trapezium is connected to the first metacarpal bone of the thumb and supports movement of the thumb relative to the remainder of the hand. This joint is susceptible to osteoarthritis that results in significant degradation of the use of the thumb in opposition to the fingers. Gripping becomes extremely painful.

Treatment of arthritis of the trapeziometacarpal joint includes joint arthroplasty, arthrodesis, and arthroscopic debridement among others. When arthroplasty is employed, recovery is aided by the proper positioning of the joint, and specifically the maintenance of the relationship between the first and second metacarpal bones during healing of the joint.

The use of sutures or other tethers to fix the position of one metacarpal relative to the other is known in the art. A securing tether is passed through a passageway formed through the cortex of adjacent metacarpals and is then secured to a plate positioned against the cortex of the metacarpal and cinched to secure the position of a first metacarpal relative to a second metacarpal. In some situations, the tether must be positioned in the plate during the surgical procedure after the tether has passed through the passageway. This approach may result in the tether being soiled by fluids and tissues present in the surgical site, thereby hindering the ability of the surgeon to position the tether in engagement with the plates.

SUMMARY

The present application discloses one or more of the features recited in the appended claims and/or the following features which alone or in any combination, may comprise patentable subject matter.

According to a first aspect of the present disclosure, a method for carpometacarpal fixation may include positioning a drill guide by advancing the drill guide from the dorsal-ulnar aspect of the second metacarpal to the base of the first metacarpal. The method also may include advancing, radial to ulnar, a cannulated drill over the drill guide. The method further may include removing the drill guide. The method still further may include advancing a suture guide through the cannulated drill, radial to ulnar. The method yet further may include inserting a suture into the suture guide. The method still further may include withdrawing the suture guide such that suture material is exposed on both the ulnar side of the second metacarpal and the radial side of the first metacarpal. The method also yet further may include fixing the suture to stabilize the relation between the first and second metacarpals.

In some embodiments, the method may also include positioning a second anchor plate to seat against the second metacarpal. The method may include positioning a first anchor plate to seat against the second metacarpal. The method may yet further include separating the first anchor plate from the suture guide.

The method may still further include positioning the suture such that a second suture loop engages the first anchor plate and the free ends of the suture are accessible at the radial side of the second metacarpal.

The method may still yet further include reducing the distance between the second metacarpal and the first metacarpal by reducing an operable length of the suture by pulling on second and second free ends of the suture. The method may also include positioning the suture such that a second suture loop engages the second anchor plate.

In some embodiments, the method may include removing the cannulated drill.

According to another aspect of the present disclosure, a method for carpometacarpal fixation may include positioning a drill guide by advancing the drill guide from the ulnar side of the second metacarpal to the base of the first metacarpal. The method may also include advancing a cannulated drill bit over the drill guide in a radial to ulnar direction. The method may include removing the drill bit. The method may still further include advancing a cannula over the drill guide through the first and second metacarpals in a radial to ulnar direction. The method may still further include removing the drill guide. The method may also further include advancing a suture guide through the cannula in a radial to ulnar direction. The method may also include inserting a suture into the suture guide. The method may still include fixing the suture to stabilize the relation between the first and second metacarpals.

The method may further include positioning a first anchor plate to seat against the first metacarpal. The method may also include positioning a second anchor plate to seat against the second metacarpal. The method may still also include separating the second anchor plate from the suture guide.

In some embodiments, the method may include positioning a first anchor plate to seat against the first metacarpal. The method may also include positioning the suture such that a first suture loop engages the first anchor plate and the free ends of the suture are accessible at the ulnar side of the second metacarpal.

In some embodiments, the method may include reducing the distance between the first metacarpal and the second metacarpal by reducing an operable length of the suture by pulling on the first and second free ends of the suture.

The method may also include positioning the suture such that a second suture loop engages the second anchor plate.

The method may still further include removing the cannula.

According to yet another aspect of the present disclosure, an assembly for carpometacarpal fixation may include a suture guide. The suture guide may include a stem and a first anchor plate frangibly secured to the stem. The first anchor plate may include a body and a plurality of through holes formed in the body. The assembly may further include second anchor plate. The second anchor plate may include a plurality of through holes formed in the second anchor plate. The assembly may still also include a tether engaged with the second anchor plate and the first anchor plate.

In some embodiments, the tether is adjustable to vary the distance between the anchor plates.

The tether may include a first loop that is engaged with the second anchor plate with the first loop extending through a first of the plurality of through holes in the second anchor plate over a portion of the second anchor plate and through a second of the plurality of through holes in the second anchor plate.

The tether may also include a second loop that is engaged with the first anchor plate with the second loop extending through a first of the plurality of through holes in the first anchor plate over a portion of the first anchor plate and through a second of the plurality of through holes in the first anchor plate.

In some embodiments, the tether may include a third loop that is engaged with the second anchor plate with the third loop extending through a first of the plurality of through holes in the second anchor plate over a portion of the second anchor plate and through a second of the plurality of through holes in the second anchor plate. The first anchor plate may comprise an oblong plate and the second anchor plate may comprise a round plate in some embodiments.

Additional features and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

Figure 1:
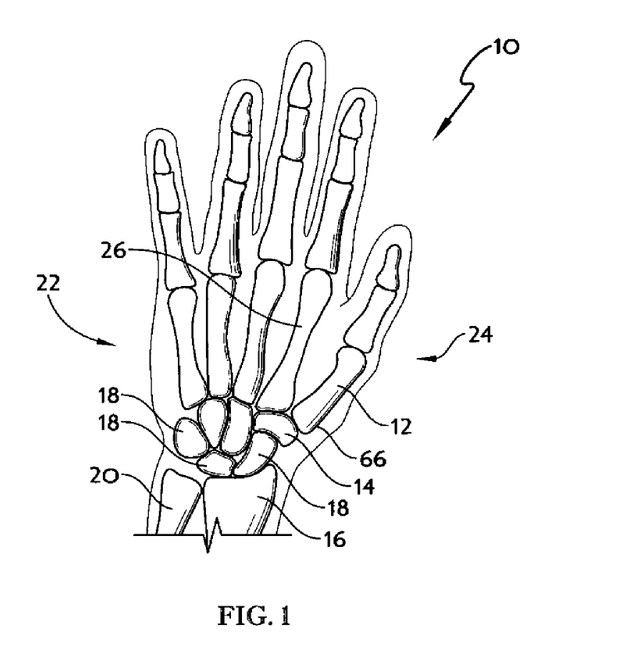
FIG. 1 is a diagrammatic representation of the bone structure of the human hand.

As shown in FIG. 1, in a human hand 10, the first metacarpal 12 (of the thumb) engages the trapezium 14, which is a carpal bone structure. The first metacarpal 12 is positioned on the medial side of the hand 10 in general alignment with the radius 16. The carpal bones 18 are supported by the radius 16 and the ulna 20. For purposes of this discussion, reference to the term "ulnar" will refer to the side 22 of the hand 10 that engages the ulna and "radial" will refer to the side 24 of the hand 10 that engages the radius. The reference to sides and directions are for orientation in understanding the procedures described below.

Figure 2:
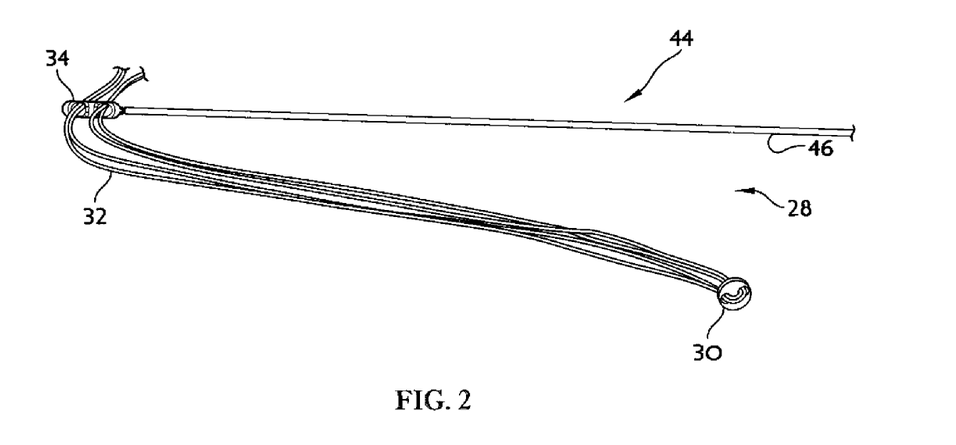
FIG. 2 is a perspective view of an assembly for fixation of a carpometacarpal relationship.

The present application discloses a method and apparatus for fixation of the first metacarpal 12 relative to the trapezium 14 by using an assembly 28 (shown in FIG. 2) to secure the first metacarpal 12 relative to the second metacarpal 26. Referring to FIG. 2, the assembly 28 includes a first anchor plate 34 that may be seated against the cortex of one of the metacarpals when the assembly 28 is installed. The assembly 28 also includes a tether 32, illustratively embodied as a suture material, which secures the first anchor plate 34 to a second anchor plate 30 that may be positioned against the cortex of a second metacarpal with the tether 32 extending between the metacarpals to maintain the spacing between the metacarpals or stabilize the metacarpal following removal or partial resection of the trapezium.

Figure 4:
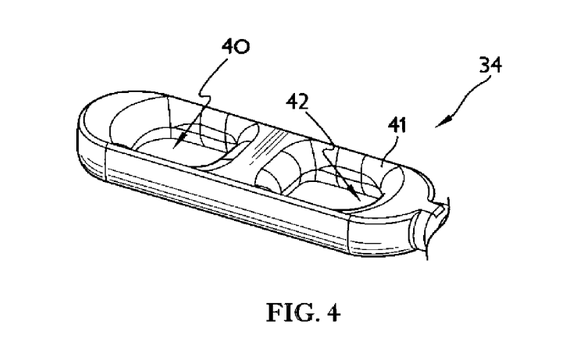
FIG. 4 is a perspective view of a second anchor plate of the assembly of FIG. 2.

As shown in FIG. 4, the first anchor plate 34 has a generally oblong body 41 with two through holes 40 and 42 formed in the first anchor plate 34. In the illustrative embodiment, the first anchor plate 34 comprises a titanium alloy, Ti-6AL-4V. It should be understood that other titanium alloys or other materials might be used to form the first anchor plate 34 as well.

Figure 3:
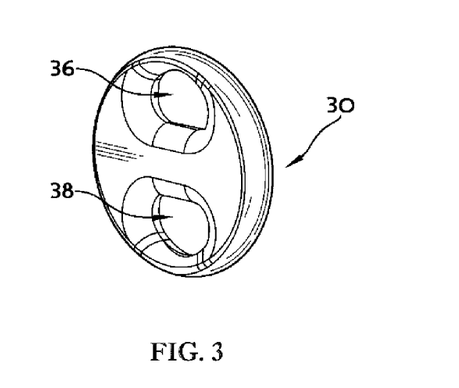
FIG. 3 is a perspective view of a first anchor plate of the assembly of FIG. 2.

As shown in FIG. 3, the second anchor plate 30 has a generally circular or round shape with two through holes 36 and 38 formed in the second anchor plate 30. In the illustrative embodiment, the second anchor plate 30 comprises a titanium alloy, Ti-6AL-4V. It should be understood that other titanium alloys or other materials might be used to form the second anchor plate 30 as well.

Figure 5:
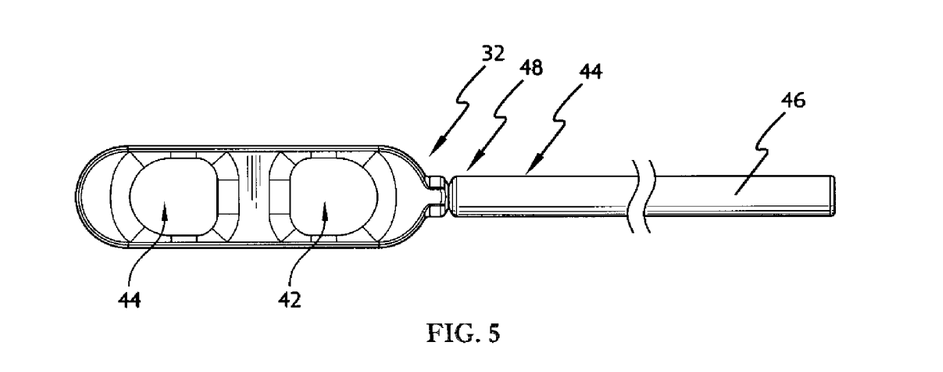
FIG. 5 is a perspective view of a suture guide of the assembly of FIG. 2.

Referring now to FIG. 5, a suture guide 44 includes a stem 46 with the second anchorplate 34 connected to the stem 46 through a frangible connection 48 which is configured to permit the second anchor plate 34 to be manually separated from the stem 46.

The assembly 28 is used to stabilize the first metacarpal 12 following partial or complete excision of the trapezium, whether excision of the trapezium is performed in an open or arthroscopic procedure. The assembly 28 may be used in conjunction with or without a biologic reconstruction of the ligament 90 at the base of the first metacarpal 12 to repair carpometacarpal arthritis or instability as preferred by the surgeon.

Figure 6:
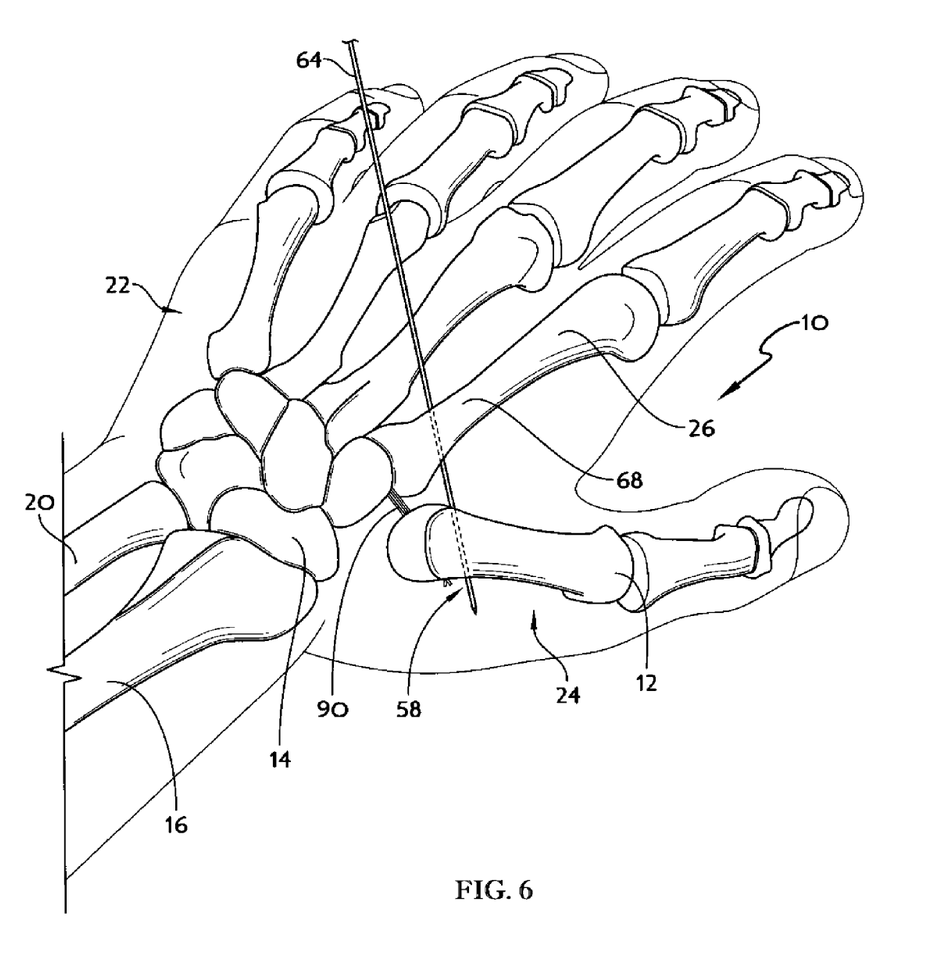
FIG. 6 is a diagrammatic view of a portion of the skeletal hand with a drill guide inserted through the first and second metacarpals.
Figure 11:
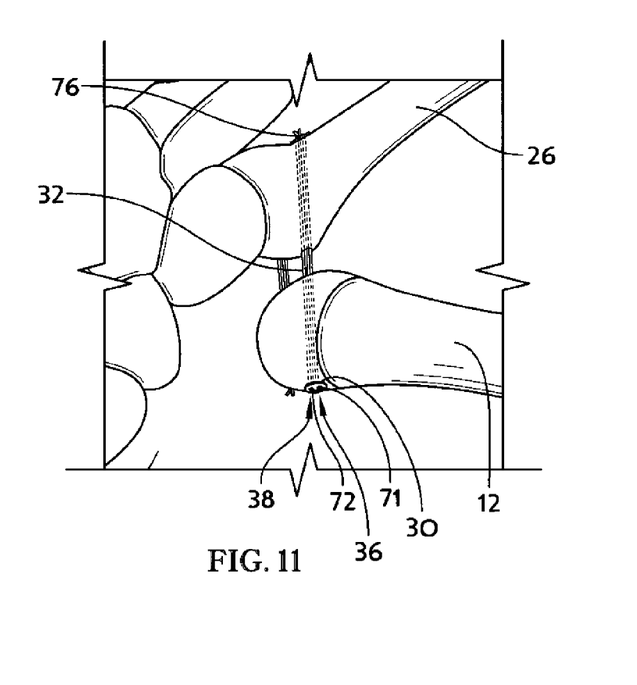
FIG. 11 is a diagrammatic view similar to FIG. 10, the second plate separated from the stem of the suture guide and the assembly secured to fix the position of the first metacarpal relative to the second metacarpal.

In one approach, the assembly 28 is positioned with a knot 76 securing the second anchor plate 34 on the ulnar side 22 of the second metacarpal 26 as shown in FIG. 11. The procedure includes advancing a 1.3-millimeter Kirschner wire 64 from the dorsal-ulnar aspect of the second metacarpal 26 to an exit point 58 at the base of the first metacarpal 12 as shown in FIG. 6. The Kirschner wire is driven approximately 3 centimeters beyond the cortex of the cortex of the first metacarpal 12. The Kirschner wire 64 is positioned under fluoroscopy with the exit point 58 positioned about 5-10 millimeters distal from the basal joint surface. The Kirschner wire is centrally positioned in the sagittal plane of each of the first metacarpal 12 and second metacarpal 26. Once the Kirschner wire 64 is placed, the exit point 58 is exposed with a 7-10 millimeter incision and blunt dissection to expose the cortex of the first metacarpal 12.

Figure 7:
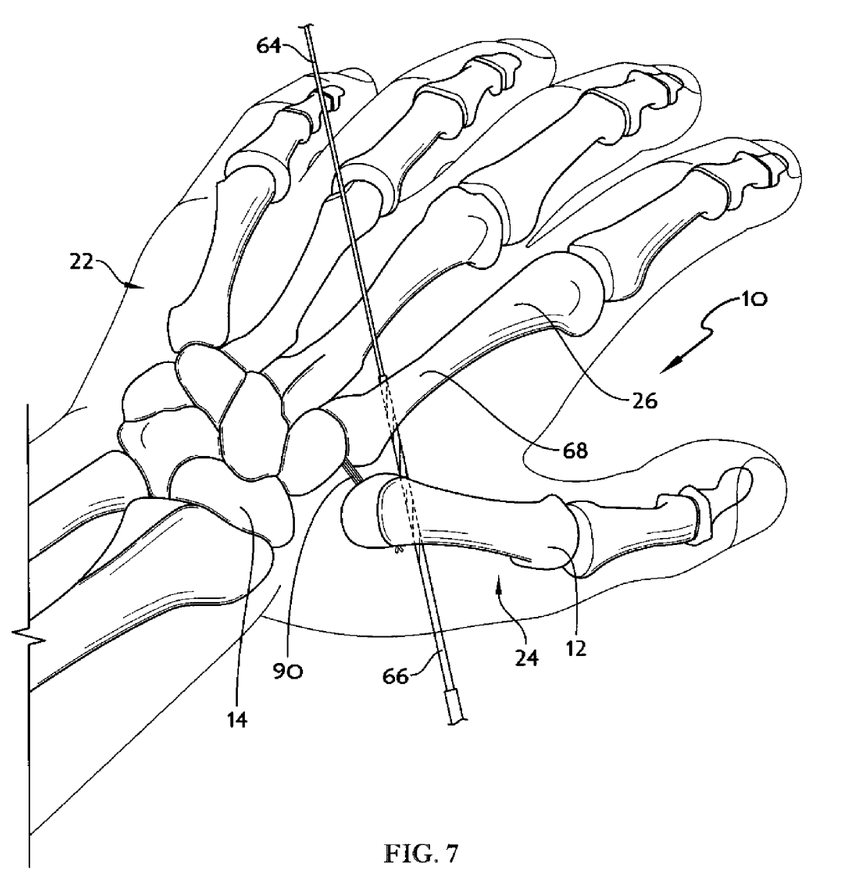
FIG. 7 is a diagrammatic view similar to FIG. 6, FIG. 7 including a cannulated drill bill advanced over the drill guide.
Figure 8:
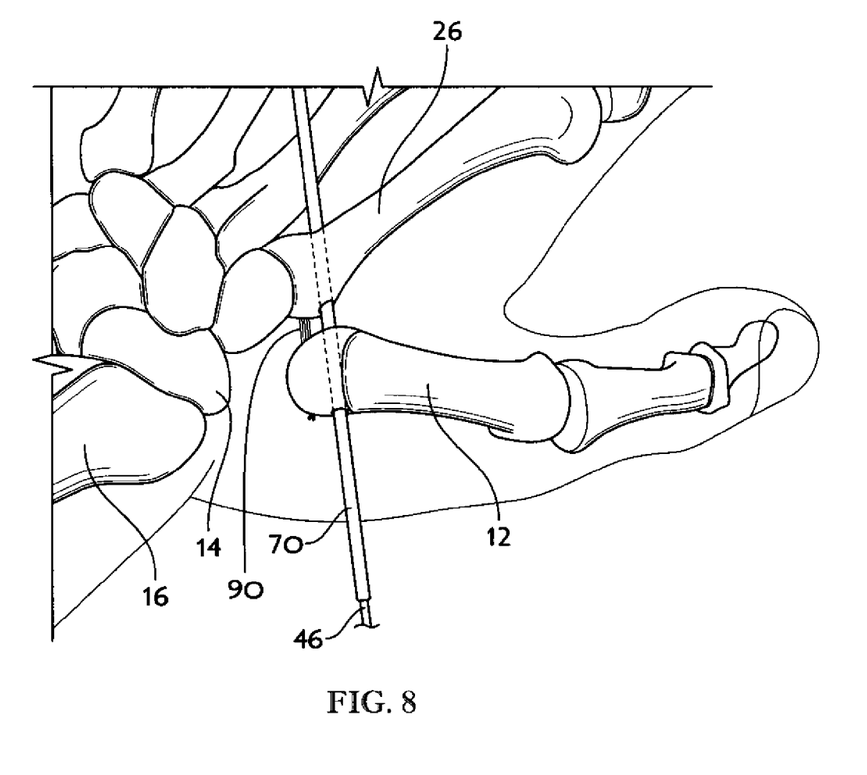
FIG. 8 is a diagrammatic view similar to FIG. 7, the hand of FIG. 8 having a cannula positioned through the first and second metacarpals.
Figure 9:
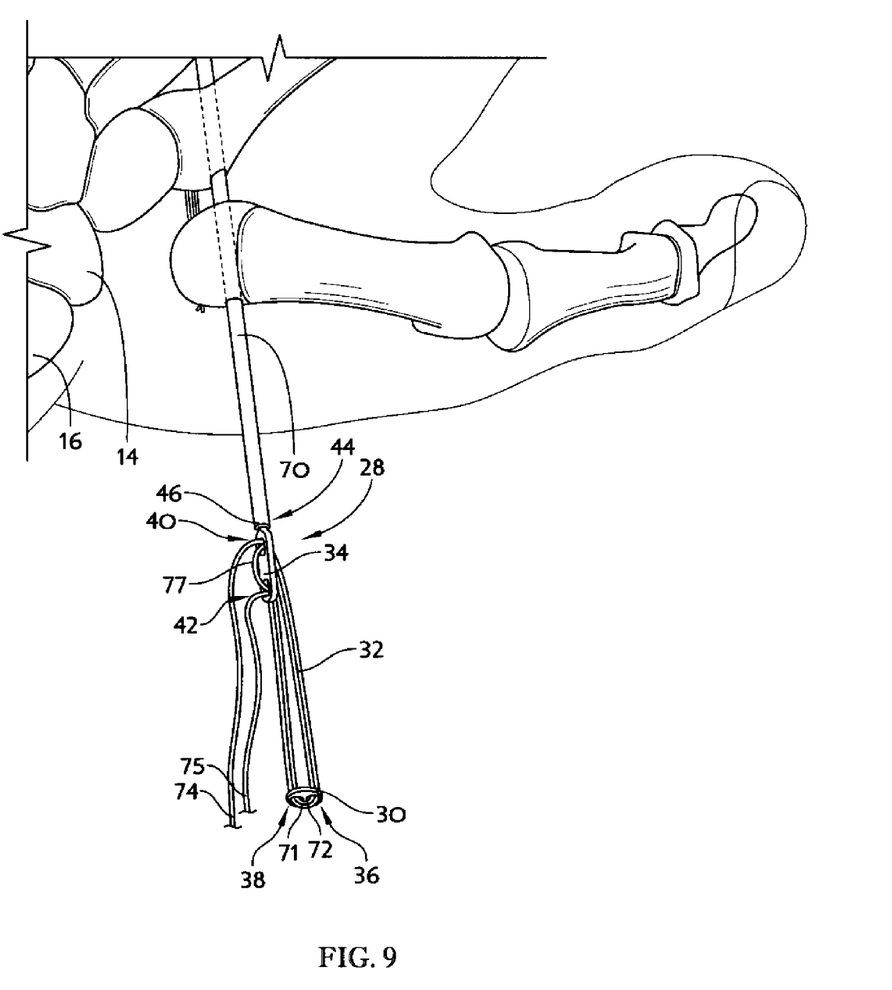
FIG. 9 is a diagrammatic view of a portion of a skeletal hand with a stem of the suture guide of FIG. 5 positioned in the cannula of FIG. 8.

Referring now to FIG. 7, a 2.7 millimeter cannulated drill bit 66 is positioned over the Kirschner wire 64 on the radial side 24 of the first metacarpal 12 and driven radial to ulnar, exiting the ulnar cortex 68 of the second metacarpal 26 as shown in FIG. 7. Referring now to FIG. 8, the drill bit 66 is withdrawn, with the Kirschner wire 64 remaining in position. A cannula embodied as a PTFE tube 70 is advanced over the Kirschner wire 64 through the first metacarpal 12 and the second metacarpal 26 as shown in FIG. 8. Referring now to FIG. 9, the Kirschner wire 64 is removed and the stem 46 of the suture guide 44 is advanced through the tube 70 radial to ulnar with the suture 32 positioned through the through holes 36 and 38 of the first plate 30. It should be understood that in some embodiments, the suture guide 44 could be advanced through the tube 70 in an ulnar to radial direction. Two loops 71 and 72 engage the first anchor plate 30 and two free ends 74 and 75 positioned in the holes 40 and 42 of the second anchor plate 34. A loop 77 passes over the body 41 of the second plate 34.

Figure 10:
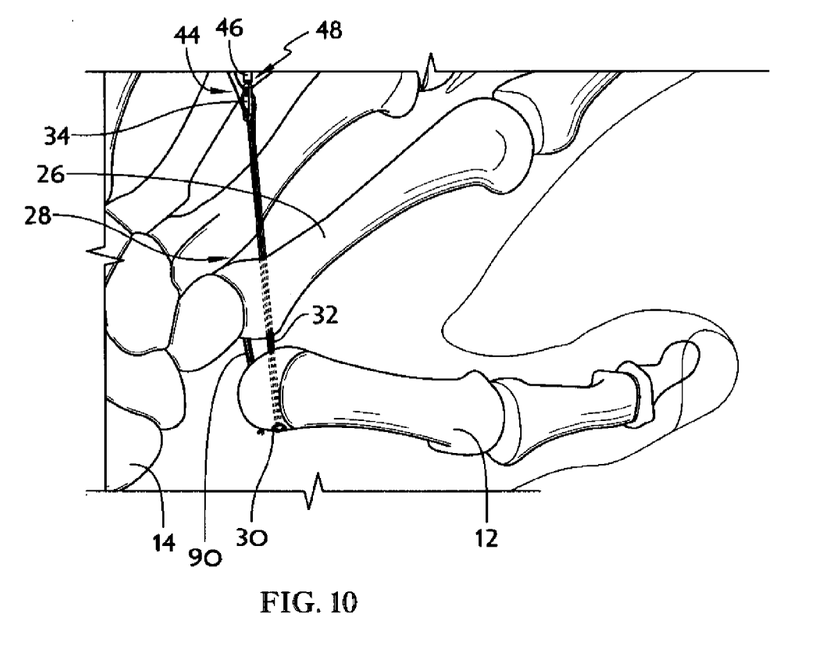
FIG. 10 is a diagrammatic view with the assembly of FIG. 2 placed on the hand such that the suture guide is positioned on the ulnar side of the second metacarpal and the first anchor plate is positioned on the radial side of the first metacarpal.

Once the suture guide 44 has been advance through the tube 70, the tube 70 is removed from the ulnar side 22 as shown in FIG. 10. The first anchor plate 30 is then positioned to seat against the first metacarpal 12. The stem 46 of the suture guide 44 is manually removed from the second anchor plate 34 by snapping the frangible connection 48 and discarding the stem 46. The first anchor plate 30 is positioned against the cortex of the first metacarpal 12 and the second anchor plate 34 is positioned against the cortex of the second metacarpal 26 without impinging on any other tissues. The suture 32 is tensioned by alternately pulling each strand is small increments until the desired reduced position of the first metacarpal 12 is achieved. The second anchor plate 34 is then secured with a multiple surgeon's knot 76 as shown in FIG. 11.

Following closure of the surgical sites, the joint is splinted. After one week, the splint, dressings, and sutures are removed and the first metacarpal 12 is splinted with a molded splint in a slightly abducted position. The splint is discontinued at four weeks post operative and progressive physical therapy is employed.

Figure 12:
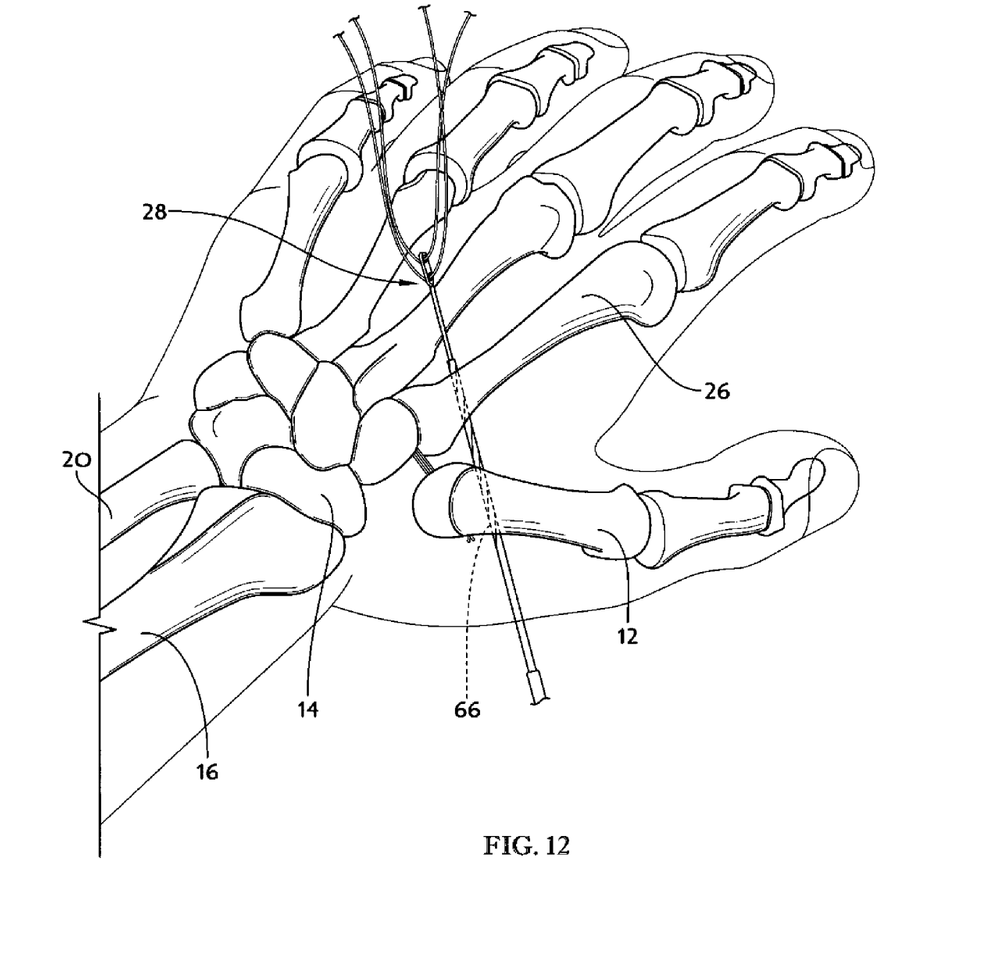
FIG. 12 is a diagrammatic view similar to FIG. 7, the stem of the suture guide of FIG. 5 positioned in the cannulated drill.
Figure 13:
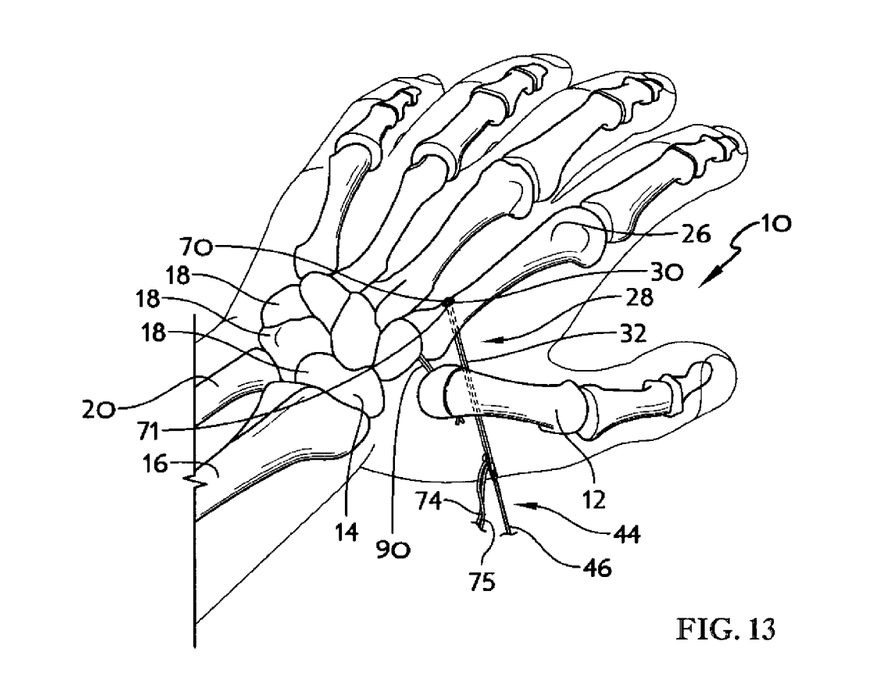
FIG. 13 is a diagrammatic view similar to FIG. 12, the cannulated drill removed from the hand and the suture guide advanced through a passageway formed in two metacarpals so that the first plate is positioned on the ulnar side of the second metacarpal.
Figure 14:
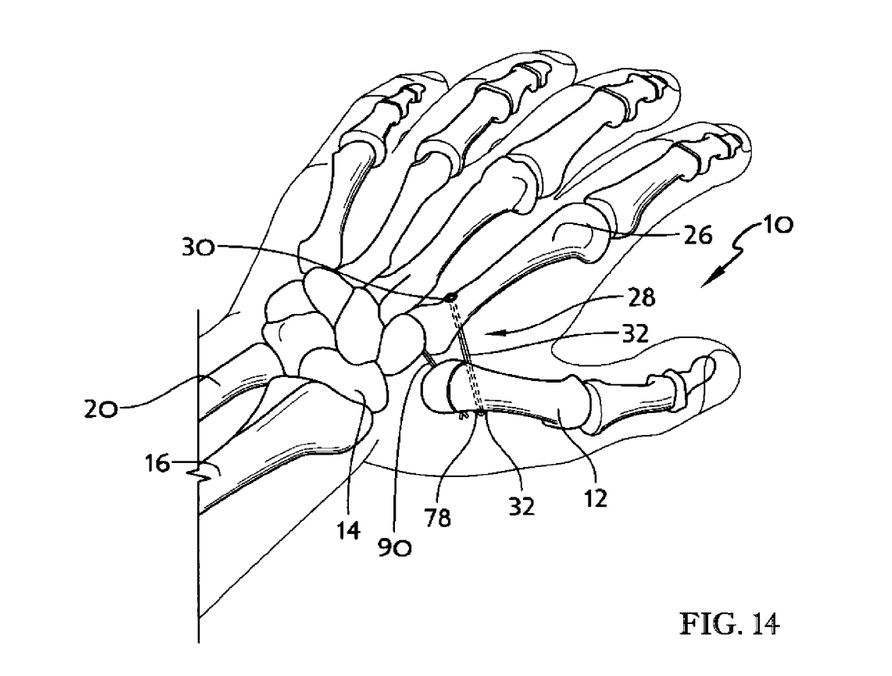
FIG. 14 is a diagrammatic view similar to FIG. 11, the first plate of the assembly positioned on the ulnar side of the second metacarpal, the second plate separated from the stem of the suture guide, and the assembly secured to fix the position of the first metacarpal relative to the second metacarpal.

In another approach, a knot 78 is positioned on the radial side 24 of the first metacarpal 12 as shown in FIG. 14. In this approach, prior to removal of the cannulated drill bit 70, the Kirschner wire 64 is removed and the stem 46 of the suture guide 44 is then inserted through the cannula of the drill bit 70 from the ulnar side 22 as shown in FIG. 12. The cannulated drill bit 70 is then removed from the radial side 24 with the stem 46 in place. The suture 32 positioned through the through holes 36 and 38 of the first plate 30. Two loops 71 and 72 engage the first anchor plate 30 and two free ends 74 and 75 positioned in the holes 40 and 42 of the second anchor plate 34. A loop 77 passes over the body 41 of the second plate 34.

Once the cannulated drill bit 80 is removed, the suture guide 44 is then advanced such that the second anchor plate 34 exits the radial side 24 of the cortex of the first metacarpal 12. The second anchor plate 34 is positioned on the ulnar side 22 of the cortex of the second metacarpal 26. The stem 46 of the suture guide 44 is manually removed from the second anchor plate 34 by snapping the frangible connection 48 and discarding the stem 46. The second anchor plate 34 is positioned against the cortex of the first metacarpal 12. The suture 32 is tensioned by alternately pulling each strand in small increments until the desired reduced position of the first metacarpal 12 is achieved. The second anchor plate 34 is then secured with a multiple surgeon's knot 78.

Following closure of the surgical sites, the joint is splinted. After one week, the splint, dressings, and sutures are removed and the first metacarpal 12 is splinted with a molded splint in a slightly abducted position. The splint is discontinued at four weeks post operative and progressive physical therapy is employed.

Although the invention has been described with reference to the preferred embodiments, variations and modifications exist within the scope and spirit of the invention as described and defined in the following claims.

The invention claimed is:

1. A method for carpometacarpal fixation comprising
   positioning a drill guide by advancing the drill guide from the ulnar side of the second metacarpal to the base of the first metacarpal,
   advancing a cannulated drill over the drill guide,
   removing the drill guide,
   advancing a suture guide into the cannulated drill,
   inserting a suture into the suture guide,
   withdrawing the suture guide such that suture material is exposed on both the ulnar side of the second metacarpal and the radial side of the first metacarpal
   separating a first anchor plate from the suture guide, and
   fixing the suture to stabilize the relation between the first and second metacarpals.

2. The method of claim 1, further comprising positioning a second anchor plate to seat against the second metacarpal.

3. The method of claim 1, further comprising positioning the first anchor plate to seat against the first metacarpal.

4. The method of claim 3, further comprising separating the first anchor plate from the suture guide by fracturing a frangible connection between the first anchor plate and the remainder of the suture guide.

5. The method of claim 4, further comprising positioning a second anchor plate to seat against the second metacarpal.

6. The method of claim 5, further comprising positioning the suture such that a first suture loop engages the second anchor plate and the free ends of the suture are accessible at the radial side of the first metacarpal.

7. The method of claim 6, further comprising reducing the distance between the first metacarpal and the second metacarpal by reducing an operable length of the suture by pulling on first and second free ends of the suture.

8. The method of claim 7, further comprising positioning the suture such that a second suture loop engages the first anchor plate.

9. The method of claim 8, further comprising removing the cannulated drill.

10. The method of claim 1, further comprising removing the cannulated drill.

11. A method for carpometacarpal fixation comprising
    positioning a drill guide by advancing the drill guide from the ulnar side of the second metacarpal to the base of the first metacarpal,
    advancing a cannulated drill over the drill guide,
    removing the drill,
    advancing a cannula over the drill guide through the first and second metacarpals,
    removing the drill guide,
    advancing a suture guide through the cannula radial to ulnar,
    inserting a suture into the suture guide,
    separating a first anchor plate from the suture guide, and
    fixing the suture to stabilize the relation between the first and second metacarpals.

12. The method of claim 11, further comprising positioning a second anchor plate to seat against the first metacarpal.

13. The method of claim 11, further comprising positioning the second anchor plate to seat against the second metacarpal.

14. The method of claim 13, further comprising separating the first anchor plate from the suture guide by fracturing a frangible connection between the first anchor plate and the remainder of the suture guide.

15. The method of claim 14, further comprising positioning a second anchor plate to seat against the first metacarpal.

16. The method of claim 15, further comprising positioning the suture such that a first suture loop engages the second anchor plate and the free ends of the suture are accessible at the ulnar side of the second metacarpal.

17. The method of claim 16, further comprising reducing the distance between the first metacarpal and the second metacarpal by reducing an operable length of the suture by pulling on the first and second free ends of the suture.

18. The method of claim 17, further comprising positioning the suture such that a second suture loop engages the first anchor plate.

19. The method of claim 18, further comprising removing the cannula.

20. The method of claim 11, further comprising removing the cannula.

\* \* \* \* \*